(12) United States Patent
Ryu et al.

(10) Patent No.: US 11,578,051 B2
(45) Date of Patent: Feb. 14, 2023

(54) THIOPHENE CARBOXAMIDE DERIVATIVE AND PLANT DISEASE CONTROL AGENT COMPRISING SAME

(71) Applicants: KOREA RESEARCH INSTITUTE OF CHEMICAL TECHNOLOGY, Daejeon (KR); FARMHANNONG CO., LTD, Seoul (KR)

(72) Inventors: Jae Wook Ryu, Daejeon (KR); Hyun Suk Yeom, Daejeon (KR); Myeong Su Shin, Daejeon (KR); In Young Oh, Daejeon (KR); Ki-Ju Park, Nonsan-si (KR); Min-Young Song, Nonsan-si (KR); Do-Hyoung Kim, Nonsan-si (KR); Han-Young Lee, Nonsan-si (KR); Kyung-Jin Jun, Nonsan-si (KR)

(73) Assignees: KOREA RESEARCH INSTITUTE OF CHEMICAL TECHNOLOGY, Daejeon (KR); FARMHANNONG CO., LTD, Seoul (KR)

( * ) Notice: Subject to any disclaimer, the term of this patent is extended or adjusted under 35 U.S.C. 154(b) by 0 days.

(21) Appl. No.: 17/283,196

(22) PCT Filed: Oct. 7, 2019

(86) PCT No.: PCT/KR2019/013131
§ 371 (c)(1),
(2) Date: Apr. 6, 2021

(87) PCT Pub. No.: WO2020/076035
PCT Pub. Date: Apr. 16, 2020

(65) Prior Publication Data
US 2021/0347755 A1    Nov. 11, 2021

(30) Foreign Application Priority Data
Oct. 8, 2018   (KR) .................. 10-2018-0119984

(51) Int. Cl.
*C07D 333/38*   (2006.01)
*A01N 43/10*   (2006.01)

(52) U.S. Cl.
CPC .......... *C07D 333/38* (2013.01); *A01N 43/10* (2013.01)

(58) Field of Classification Search
CPC combination set(s) only.
See application file for complete search history.

(56) References Cited

U.S. PATENT DOCUMENTS

| 2004/0039043 A1* | 2/2004 | Elbe ............... A01N 43/40 548/369.7 |
| 2005/0182120 A1 | 8/2005 | Elbe et al. |
| 2008/0085924 A1 | 4/2008 | Dunkel et al. |
| 2015/0141247 A1* | 5/2015 | Maechling ............. A01N 43/56 504/116.1 |

FOREIGN PATENT DOCUMENTS

| WO | 02/08197 A1 | 1/2002 |
| WO | 2004/054982 A1 | 7/2004 |
| WO | 2007/072999 A1 | 6/2007 |
| WO | 2007/128756 A1 | 11/2007 |
| WO | 2013/167550 A1 | 11/2013 |
| WO | 2017/042142 A1 | 3/2017 |
| WO | WO 2017-042142 * | 3/2017 |

OTHER PUBLICATIONS

International Search Report dated Jan. 17, 2020 for corresponding international application No. PCT/KR2019/013131.
Written Opinion dated Jan. 17, 2020 for corresponding International Patent Application No. PCT/KR2019/013131.

* cited by examiner

*Primary Examiner* — Valerie Rodriguez-Garcia
(74) *Attorney, Agent, or Firm* — Hauptman Ham, LLP

(57) ABSTRACT

The present invention provides a thiophene carboxamide compound of the following General Formula (I), which is a novel fluorine-substituted biphenyl carboxamide-based compound, and provides a useful compound, as an agricultural and horticultural plant disease control agent, exhibiting an excellent control effect at a low dose.

General Formula I

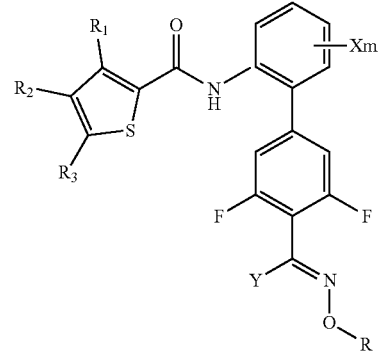

wherein, R, R1, R2, R3, Xm, and Y are each as defined in the specification.

6 Claims, No Drawings

THIOPHENE CARBOXAMIDE DERIVATIVE AND PLANT DISEASE CONTROL AGENT COMPRISING SAME

CROSS-REFERENCE TO RELATED APPLICATION

The present application is a national stage filing under 35 U.S.C. § 371 of PCT application number PCT/KR2019/013131 filed on Oct. 7, 2019 which is based upon and claims the benefit of priorities to Korean Patent Application No. 10-2018-0119984, filed on Oct. 8, 2018, in the Korean Intellectual Property Office, which are incorporated herein in their entireties by reference.

TECHNICAL FIELD

The present invention relates to a fluorine-substituted biphenyl thiophene carboxamide- based compound derivative, a salt thereof, a structural isomer thereof, and an agricultural and horticultural plant disease control agent comprising the same as an active ingredient.--

BACKGROUND ART

It is already known that many carboxamide-based compounds have microbial control effects (e.g., WO2002/008197 A1, WO 2004/054982 A1, WO 2013/167550 A1, and WO 2017/042142 A1). The control activity of these substances is good, but is often not satisfactory.

DISCLOSURE

Technical Problem

Plant disease control agents for agricultural and horticultural use disclosed in the conventional technology mentioned in the above example do not show a practical level of control activity, so further research is still required. In particular, it is limited in its activity for controlling powdery mildew. In addition, recent crop protection agents strongly require environmentally friendly compounds, and thus, plant disease control agents for agricultural and horticultural use, which exhibit high activity in low doses, are increasingly demanded.

Technical Solution

As a result of diligently researching by the present inventors to solve the above problems, it was found, thereby completing the present invention that the fluorine-substituted thiophene biphenyl carboxamide-based compound derivatives, structural isomers, and salts thereof represented by the General Formula (I) of the present invention have a high fungicidal spectrum against powdery mildew even at a low dose, in addition to showing excellent control effect as a plant disease control agent for agricultural and horticultural use. That is, the present invention relates to a fluorine-substituted thiophene biphenyl carboxamide-based compound or a salt thereof represented by the following <General Formula 1>, a method for preparing them, and a plant disease control agent for agricultural and horticultural use comprising them.

The present invention is related to 1) a fluorine-substituted biphenyl carboxamide derivative, or a structural isomer or salt thereof represented by the following General Formula:

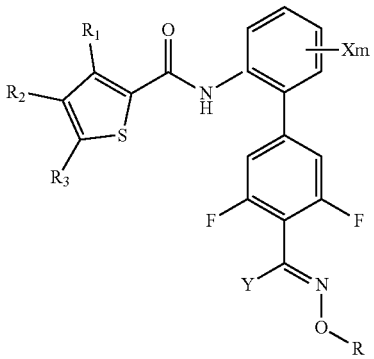

(I)

In the above Formula,

Y is a hydrogen atom or a (C1~C4)alkyl;

X is a halogen atom or a (C1~C4)alkyl;

m is an integer of 0~2;

R is a hydrogen atom, (C1~C6)alkyl, (C2~C6)alkenyl, (C2~C6)alkynyl, (C1~C6)alkyl which may be substituted by 1 to 5 halogen atoms, (C1~C3)alkyl which may be substituted with (C3~C6)cycloalkyl, (C1~C3)alkyl which may be substituted with phenyl or pyridine, phenyl(C1~C3)alkyl (which may be substituted with a halogen atom), phenyl (C1~C3)alkyl which may be substituted with (C1~C4)alkyl, or phenyl(C1~C3)alkyl which may be substituted with (C1~C4)alkoxy;

R1 is a halogen, (C1~C4)alkyl, or (C1~C4)alkyl substituted by 1 to 3 halogen atoms, and R2 and R3 are each independently hydrogen, (C1~C4)alkyl, or halogen.

2) in said 1),

Y is a hydrogen atom; m is 0; R is (C1~C6)alkyl, (C2~C6)alkenyl, (C2~C6)alkynyl, (C1~C6)alkyl which may be substituted by 1 to 5 halogen atoms, (C1~C3)alkyl which may be substituted with (C3~C6)cycloalkyl, (C1~C3) alkyl which may be substituted with phenyl or pyridine, phenyl(C1~C3)alkyl (which may be substituted with a halogen atom), phenyl(C1~C3)alkyl which may be substituted with (C1~C4)alkyl, or phenyl(C1~C3)alkyl which may be substituted with (C1~C4)alkoxy; R1 is (C1~C4)alkyl or (C1~C4)alkyl substituted with 1 to 3 halogen atoms; and R2 and R3 are a hydrogen atom.

3) in said 1)

Y is a hydrogen atom, m is 0, R is (C1~C6)alkyl or (C1~C4)alkyl which may be substituted by 1 to 3 halogen atoms; R1 is methyl, and R2 and R3 are a hydrogen atom.

4) a structural isomer of said 2);

5) a plant disease control agent for agricultural and horticultural use, characterized in that it comprises the compound described in said 1) to 4) as an active ingredient; or 6) a method for controlling a plant disease, characterized in that the agent of said 5) is applied to a plant or soil.

Specific Details for the Implementation of the Invention

According to the present invention, a novel fluorine-substituted thiophene biphenyl carboxamide of the following General Formula (I) was found.

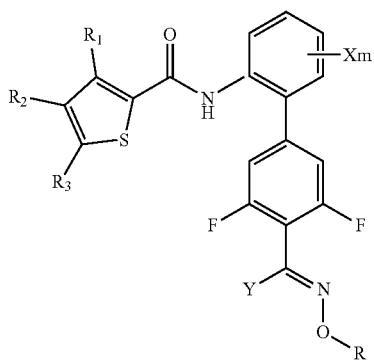

(I)

In the above Formula, the definition of the General Formula (I) of the present invention is as follows:

The "halogen atom" includes a fluorine atom, a chlorine atom, a bromine atom, and an iodine atom.

Example of "(C1~C6)alkyl which may be substituted by halogen atoms" includes a linear or branched alkyl group having 1 to 6 carbon atoms such as methyl, ethyl, normal propyl, isopropyl, normal butyl, isobutyl, secondary butyl, tertiary butyl, normal pentyl, neopentyl, and normalhexyl; and a linear or branched alkyl group having 1 to 6 carbon atoms substituted by one or more halogen atoms, which may be the same or different, for example, in which fluoromethyl, difluoromethyl, trifluoromethyl, perfluoroethyl, chloromethyl, bromomethyl, 1-bromoethyl, 2,3-dibromopropyl, etc. are included.

Example of "(C2~C6)alkenyl" includes a linear or branched alkenyl group having 2 to 6 carbon atoms such as vinyl, allyl, isopropenyl, 1-butenyl, 2-butenyl, 2-methyl-2-propenyl, 1-methyl-2-propenyl, 2-methyl-1-propenyl, pentenyl, and 1-hexelyl.

Example of "(C2~C6)alkynyl" includes a linear or branched alkynyl group having 2 to 6 carbon atoms such as ethynyl, 1-propynyl, 2-propynyl, 1-butynyl, 2-butynyl, 3-butynyl, 3-methyl-1-propynyl, 2-methyl-3-propynyl, pentynyl, and 1-hexynyl.

Example of the "(C1~C4)alkoxy" includes a linear or branched alkoxy group having 1 to 3 carbon atoms such as methoxy, ethoxy, normal propoxy, isopropoxy, normal butoxy, and isobutoxy.

As salts of the biphenyl thiophene carboxamide derivative represented by the General Formula (I) of the present invention, for example, inorganic acid salts such as hydrochloride, sulfate, nitrate, phosphate; organic acid salts such as acetate, fumarate, maleate, oxalate, methanesulfonate, benzenesulfonate, and paratoluenesulfonate; and salts with inorganic or organic ions such as lithium ions, sodium ions, potassium ions, calcium ions, and trimethyl ammonium can be exemplified.

Structural isomers of the thiophene biphenyl carboxamide derivative represented by the General Formula (I) of the present invention may be in the form (E) and the form (Z).

In the compound represented by the General Formula (I) of the present invention, preferably, X is chlorine atom; bromine atom; methyl; fluoromethyl; difluoromethyl; or trifluoromethyl. More preferably, X is a fluorine group.

Preferably, Y is hydrogen atom; halogen atom; or methyl. More preferably, Y is hydrogen atom.

Preferably, R is methyl; ethyl; propyl; propylene; butyl; t-butyl, phenylmethyl, 4-chlorophenylmethyl, 4-fluorophenylmethyl, fluoromethyl, trifluoromethyl, trifluoroethyl, or chloroethyl. More preferably, R is methyl or trifluoroethyl.

More preferred examples of the <Formula 1> are as follows:

(E)-N-(3',5'-difluoro-4'-((methoxyimino)methyl)-[1,1'-biphenyl]-2-yl)-3-methylthiophene-2-carboxamide, (E)-N-(4'-((ethoxyimino)methyl)-3',5'-difluoro-[1,1'-biphenyl]-2-yl)-3-methylthiophene-2-carboxamide, (E)-N-(3',5'-difluoro-4'-((isopropoxyimino)methyl)-[1,1'-biphenyl]-2-yl)-3-methylthiophene-2-carboxamide, (E)-N-(4'-((t-butoxyamino)methyl)-3',5'-difluoro-[1,1'-biphenyl]-2-yl)-3-methylthiophene-2-carboxamide, (E)-N-(4'-(((aryloxy)imino)methyl)-3',5'-difluoro-[1,1'-biphenyl]-2-yl)-3-methylthiophene-2-carboxamide, (E)-N-(3',5'-difluoro-4'-(((2,2,2-trifluoroethoxy)imino)methyl)-[1,1'-biphenyl]-2-yl)-3-methylthiophene-2-carboxamide, and (E)-N-(4'-(((benzyloxy)imino)methyl)-3',5'-difluoro-[1,1'-biphenyl]-2-yl)-3-methylthiophene-2-carboxamide.

The compound of the present invention is, for example, prepared according to the following manufacturing methods 1 and 2, but is not limited thereto.

<Manufacturing Method 1>

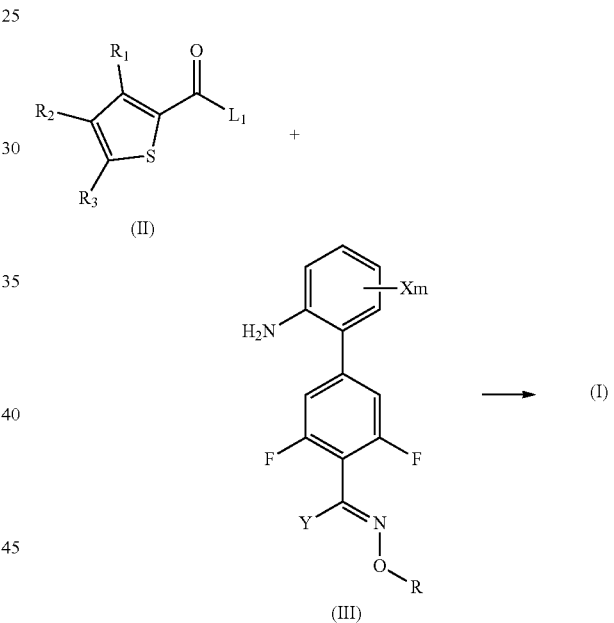

(Wherein, R, R1, R2, R3, Xm, and Y are as defined in the above formula, and L1 represents a leaving group such as a chlorine atom, a bromine atom, or an alkoxy group.)

The fluorine-substituted thiophene biphenyl carboxamide derivatives represented by the General Formula (I) can be prepared by reacting the thiophenic acid derivative represented by the General Formula (II) and the 2-aminobiphenyl derivative represented by the General Formula (III) in the presence of a base in an inert solvent. The reaction temperature in this reaction is usually in the range of about −20° C. to 120° C., and the reaction time is usually in the range of about 0.1 hour to 48 hours. The 2-aminobiphenyl derivative represented by the General Formula (III) is usually used in the range of about 0.5 to 4 times mole relative to the acid A derivative represented by the General Formula (II).

Examples of the base include inorganic bases such as sodium hydroxide, potassium hydroxide, sodium carbonate, potassium carbonate, sodium hydrogen carbonate and potassium hydrogen carbonate; acetates such as sodium acetate and potassium acetate; alkali metal alkoxides such as potassium t-butoxide, sodium methoxide, and sodium ethoxide; tertiary amines such as triethylamine, diisopropyl ethylamine, and 1,8-diazabicyclo[5.4.0]undec-7-ene; nitrogen-containing aromatic compounds such as pyridine and dimethylamino pyridine; and so on. The amount of the base is usually used in the range of about 0.5 to 5 times mole relative to the acid A derivative represented by the General Formula (II). As an inert solvent that can be used, it can be used as long as it does not significantly inhibit the reaction, and examples thereof include alcohols such as methanol, ethanol, propanol, butanol and 2-propanol; straight-chain or cyclic ethers such as diethyl ether, tetrahydrofuran, and dioxane; aromatic hydrocarbons such as benzene, toluene, and xylene; halogenated hydrocarbons such as methylene chloride, chloroform, and carbon tetrachloride; halogenated aromatic hydrocarbons such as chlorobenzene and dichlorobenzene; nitriles such as acetonitrile; esters such as ethyl acetate; and polar solvents such as N,N-dimethylformamide, N,N-dimethylacetamide, dimethyl sulfoxide, 1,3-dimethyl-2-imidazolidinone, water, and acetic acid. These inert solvents may be used alone or in combination of two or more.

<Manufacturing Method 2> chlorine atom, a bromine atom, and an iodine atom, and L3 is B(OH)$_2$ group, or B(OG2)$_2$ group (wherein, G2 may be the same or different and represents (C1~C10)alkyl, or two G2 may be bonded at the terminal to form CH$_2$CH$_2$ or C(CH$_3$)C2(CH$_3$)$_2$).

The compound of General Formula (V) can be prepared by the method of compound (I) of <Manufacturing method 1>.

The fluorine-substituted thiophene carboxamide derivatives of the present invention represented by the General Formula (VII) can be prepared by reacting the thiophene carboxamide derivative represented by the General Formula (V) with the compound represented by the General Formula (VI) in an inert solvent in the presence of a catalyst and a base. In this reaction, the reaction temperature is usually in the range of about 20° C. to 150° C., and the reaction time is usually in the range of about 0.5 to 48 hours. The compound represented by the General Formula (V) is usually used in the range of about 0.8 to 5 times mole relative to the acid A derivative represented by the General Formula (IV). As a catalyst, for example, palladium catalysts such as palladium (II) acetate, tetrakis(triphenylphosphine)palladium (0), [1,1'-bis(diphenylphosphino)ferrocene]dichloropalladium (II) methylene chloride complex, and bis(triph-

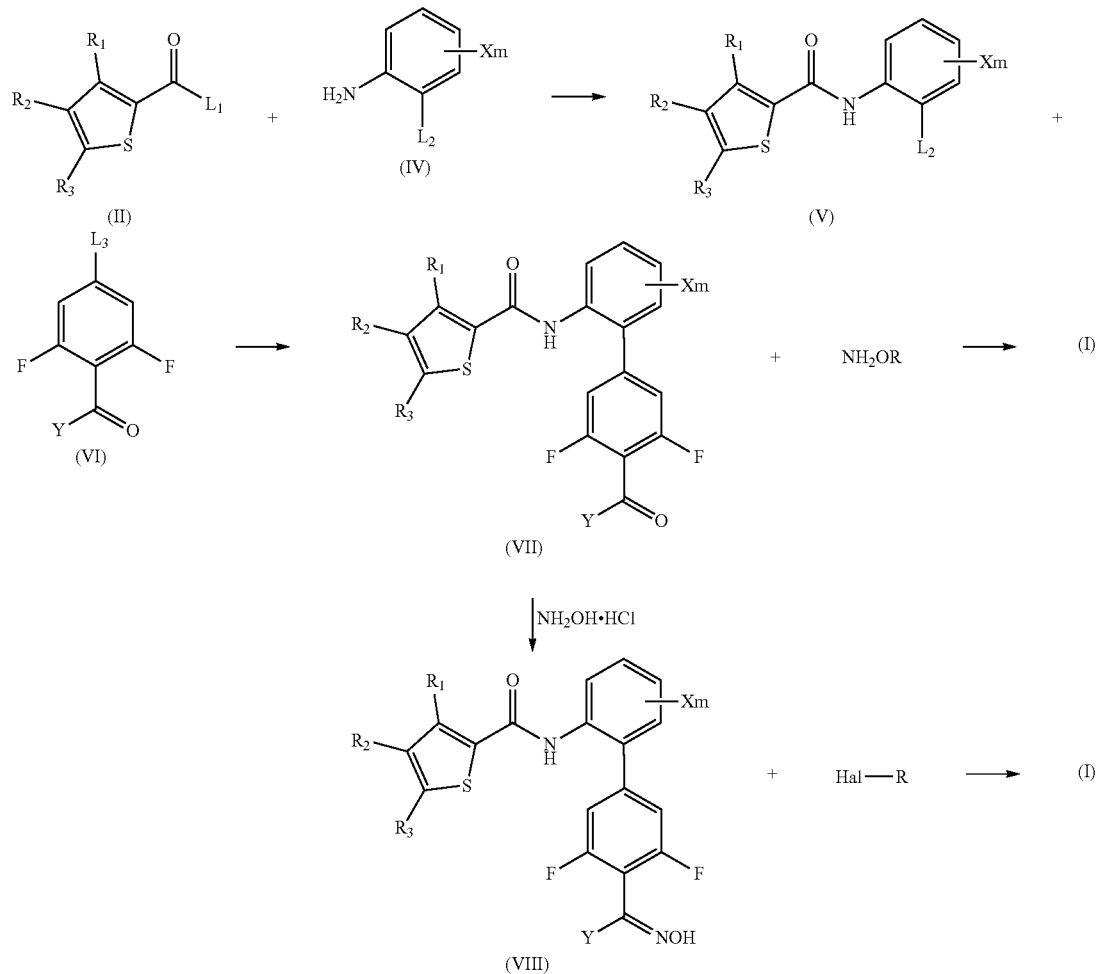

(Wherein, R, R1, R2, R3, Xm, Y, and L1 are as defined in the above formula, L2 represents a leaving group such as a enylphosphine)palladium(II) dichloride can be used. The amount of the catalyst used is in the range of about 0.001 to 0.2 times mole relative to the compound represented by the General Formula (V). Examples of the base include inorganic bases such as potassium phosphate, sodium hydroxide, potassium hydroxide, sodium carbonate, potassium carbonate, cesium carbonate, sodium hydrogen carbonate and potassium hydrogen carbonate; and acetates such as sodium acetate and potassium acetate. The amount of base used is usually in the range of about 0.5 to 10 times mole relative to the acid A derivative represented by the General Formula (IV).

In addition, the desired compound of the general formula (I) can be prepared by reacting the compound of the General Formula (VII) with an $NH_2OR$ compound. At this time, the reaction temperature in this reaction is usually in the range of about $-20°$ C. to $100°$ C., and the reaction time is usually carried out in the range of about 0.5 hours to 24 hours. The $NH_2OR$ compound is usually used in the range of about 1.0 to 5 times mole relative to the General Formula (VII) derivative. Examples of the base include inorganic bases such as potassium phosphate, sodium hydroxide, potassium hydroxide, sodium carbonate, potassium carbonate, cesium carbonate, sodium hydrogen carbonate and potassium hydrogen carbonate; and acetates such as sodium acetate and potassium acetate. The amount of base used is usually in the range of about 1.0 to 10 times mole relative to the General Formula (VI).

The compound of General Formula (VIII) can be prepared by reacting the compound of General Formula (VII) with $HN_2OH$ hydrochloride. At this time, the $HN_2OH$ hydrochloride can be prepared by a reaction for 0.5 hours to 24 hours at $-20°$ C. to $50°$ C. using 1.0 to 4 equivalents based on (VII). Compound (I) can be obtained by using L2-R having an appropriate L2 from the compound of the General Formula (VIII) by the method of <Manufacturing method 1>.

This reaction can be carried out in the presence of a phase-transfer catalyst (for example, quaternary ammonium salts such as tetrabutylammonium bromide and benzyltriethylammonium bromide, etc.) as necessary. As an inert solvent that can be used, it can be used as long as it does not significantly inhibit the reaction, and examples thereof include alcohols such as methanol, ethanol, propanol, butanol and 2-propanol; straight-chain or cyclic ethers such as diethylether, tetrahydrofuran, and dioxane; aromatic hydrocarbons such as benzene, toluene, and xylene; halogenated hydrocarbons such as methylene chloride, chloroform, and carbon tetrachloride; halogenated aromatic hydrocarbons such as chlorobenzene and dichlorobenzene; nitriles such as acetonitrile; esters such as ethyl acetate; and polar solvents such as N,N-dimethylformamide, N,N-dimethylacetamide, dimethyl sulfoxide, 1,3-dimethyl-2-imidazolinone, water, and acetic acid. Such inert solvents can be used alone, or can be used by mixing two or more types.

After completion of the reaction, a compound of interest can be obtained by a conventional method which may separate it from the reaction system. In general, said compound can be purified through precipitation and filtration of the reaction mixture in an appropriate solvent, and if necessary, said compound can be prepared by a purification method such as recrystallization, column chromatography, or the like. In the compound to be prepared, structural isomers having different melting points may be prepared. All are included in the present invention.

Representative examples and NMR data of the fluorine-substituted carboxamide derivative represented by the General Formula (I) of the present invention obtained in this way are exemplified in Table 1, but the present invention is not limited thereto.

In Table 1 below, "Me" is a methyl group, "Et" is an ethyl group, "Pr" is a propyl group, "Bu" is a butyl group, "Ph" is a phenyl group, "n-" is a normal, and "i-" represents iso, and "t-" represents tertiary.

The compound according to the present invention has a strong fungicidal activity and thus can be used to remove fungi and bacteria for controlling plant diseases in agriculture and horticulture.

In the method of controlling plant diseases, it is possible to apply the present compound to the above-ground parts of plants, propagation stems and seeds, and soil at the required concentration.

The active compound according to the present invention is a control agent for plant diseases for agricultural and horticultural use, in particular, it is possible to control plant diseases of rice, fruit trees, vegetables, and other crops and flowers.

When the compound of the present invention is used as an active ingredient of a plant disease control agent, it may be used as it is without adding other ingredients, but it is generally preferable to use it as an agrochemical formulation having a shape suitable for use according to the conventional method of pesticide preparation.

The compound according to the present invention can be used not only to control plant diseases but to protect industrial materials from invasion and destruction by unwanted microorganisms. For example, industrial materials intended to be protected by the active compound according to the present invention from change or destruction by microorganisms may be adhesive, paper, plywood, textile, leather, wood, paint, plastic products, cooling lubricants, or any other material that can become damaged or destroyed by microorganisms.

The active compound can be formulated, depending on its specific physical and/or chemical property, into solution, emulsion, suspension, powder, foam, paste, granules, aerosol, and conventional preparations such as polymers and ultrafine capsules in coating compositions for seeds, and ULV coolant and warmer.

These formulations are prepared by known methods, for example, optionally using surfactants, i.e. emulsifiers and/or dispersants and/or foaming agents, to mix the active compounds with carriers, i.e. liquid solvents, pressurized liquefied gases and/or solid pillars.

If water is used as the carrier, an organic solvent can also be used as a co-solvent.

The formulations generally comprise from 0.1 to 95% by weight, preferably from 0.5 to 90% by weight of the active compound.

The active compound according to the present invention can be used either in itself or in combination with known fungicides, bactericides, acaricides, nematodes or insecticides, for example to broaden fungicidal activity spectrum or to prevent resistance. In many cases a synergistic effect is observed, i.e. the activity of the mixture exceeds that of the individual ingredients.

The active compound may be used as such, in a form of its formulation, or in a form prepared therefrom such as ready-to-use solutions, suspensions, wettable powders, pastes, soluble powders, powders and granules. These are applied by conventional methods, for example irrigation, spraying, misting, scattering, dusting, foaming, sprinkling and the like. In addition, the active compound can be applied by the micro-volume method, or the active compound preparation or the active compound itself can be injected into the soil. Plant seeds may also be treated.

If necessary, other antimicrobial active compounds, fungicides, bactericides, herbicides, pesticides or other active compounds may be added to broaden the spectrum of activity or obtain specific effects, such as additional protection against insects. It is possible to increase the activity and activity spectrum of the active compounds used according to the present invention, or compositions, concentrates or very common formulations that can be prepared from them. These mixtures may have a broader spectrum of activity than the compounds according to the invention.

Advantageous Effects

The present invention provides a compound showing an excellent activity compared to the prior art, and in particular, having a broad control spectrum with a low dose as a plant disease control agent for agricultural and horticultural use.

MODE FOR INVENTION

Next, the present invention is specifically described with reference to Examples and Experimental Examples, but the present invention is not limited thereto unless the gist of the invention is exceeded.

MANUFACTURING EXAMPLE

Example 1

Synthesis of N-(3',5'-difluoro-4'-((methoxyimino) methyl)-[1,1'-biphenyl]-2-yl)-3-methylthiophene-2-carboxamide (Compound 1)

To a solution of N-(3',5'-difluoro-4'-formyl-[1,1'-biphenyl]-2-yl)-3-methylthiophene-2-carboxamide (2.30 g, 6.42 mmol) in 15 mL of ethanol was added sequentially methylhydroxamide hydrochloride (1.33 g, 2.5 eq) and sodium acetate trihydrate (2.21 g, 2.5 eq) at room temperature and stirred for 2 hours. After the completion of the reaction was confirmed by TLC, the organic layer was separated using ethyl acetate (100 mL) and 20 mL of water. The organic layer was dried over magnesium sulfate, and concentrated. The obtained white solid was recrystallized using ethyl ether to give the white solid 2.01 g (yield 81%).

$^1$H NMR (CDCl$_3$) δ 2.42 (s, 3H), 4.05 (s, 3H), 6.86 (d, J=5.1 Hz, 1H), 7.05 (d, J=8.9 Hz, 2H), 7.25 (m, 3H). 7.36 (t, J=6.0 Hz, 1H), 7.45 (s, 1H), 8.28 (s, 1H), 8.35 (d, J=8.3 Hz, 1H)

Example 1-1

Synthesis of N-(3',5'-difluoro-4'-formyl-[1,1'-biphenyl]-2-yl)-3-methylthiophene-2-carboxamide To a solution of N-(2-bromophenyl)-3-methylthiophene-2-carboxamide (10.2 g, 34.6 mmol) in 100 mL of dimethylformamide was added 25 mL of distilled water, followed by sequential addition of 3,5-difluoro-4-formyl phenylboronic acid (10.9 g, 1.7 eq), palladium(II) acetate (388 mg, 0.05 eq), and potassium phosphate tribasic-trihydrate (9.0 g, 1.1 eq). The reaction mixture was stirred at 85° C. for 2 hours under nitrogen conditions. After the completion of the reaction was confirmed by TLC, ethyl acetate (1000 mL) and saturated brine (100 mL) were added to the reaction mixture to separate the layers, followed by filtration through Celite. The filtrate was diluted with ethyl acetate (200 mL), and the organic layer was washed with saturated Na$_2$CO$_3$ aqueous solution (30 mL×2) and saturated brine (50 mL×2). The organic layer was dried over magnesium sulfate, and concentrated. The obtained concentrate was recrystallized using ethyl ether to give the above solid 10.9 g (88%)

$^1$H NMR (CDCl$_3$) δ 2.45 (s, 3H), 6.89 (d, 1H), 7.07 (d, 2H), 7.25 (s, 3H). 7.47 (m, 2H), 8.23 (d, 1H), 10.37 (s, 1H)

Example 1-2

Synthesis of N-(2-bromophenyl)-3-methylthiophene-2-carboxamide

To a solution of 2-bromoaniline (50.0 g, 311.3 mmol) and pyridine (25 mL, 1.0 eq) in tetrahydrofuran (300 mL) was added 3-methyl-2-thienyl chloride (50.0 g, 1.0 eq) slowly at 0° C. After 30 minutes, the mixture was stirred for an additional 3 hours at room temperature. Ethyl acetate (100 mL) and water (40 mL) were added to the reaction mixture to separate the organic layer, and the organic layer was washed sequentially with 1.0 M HCl aqueous solution (30 mL), saturated aqueous sodium hydrogen carbonate solution (30 mL), and saturated brine (50 mL). The organic layers were collected, dried over magnesium sulfate, and concentrated. The obtained concentrate was recrystallized using ethyl ether to give the above white solid 79.8 g (yield 86%).

$^1$H NMR (CDCl$_3$) δ 2.65 (s, 3H), 7.0 (m, 2H), 7.36 (m, 2H). 7.56 (d, 1H), 8.17 (brs, 1H), 8.5 (d, 1H)

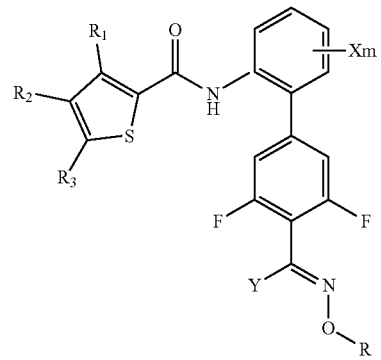

Table 1 shows NMR data of the compounds.

TABLE 1

| Compound No. | R1 | R2, R3 | Y | Xm | R | $^1$H NMR (300 MHz, Solvent) |
|---|---|---|---|---|---|---|
| 1 | Me | H | H | — | Me | (CDCl$_3$) δ 2.42 (s, 3H), 4.05 (s, 3H), 6.86 (d, J = 5.1 Hz, 1H), 7.05 (d, J = 8.9 Hz, 2H), 7.25 (m, 3H). 7.36 (t, J = 6.0 Hz, 1H), 7.45 (s, 1H), 8.28 (s, 1H), 8.35 (d, J = 8.3 Hz, 1H) |
| 2 | Me | H | H | — | t-Bu | (CDCl$_3$) δ 1.38 (s, 9H), 2.41 (s, 3H), 6.88 (d, J = 5.0 Hz, 1H), 7.01 (d, J = 8.9 Hz, 2H), 7.25 (m, 3H). 7.43 (t, J = 6.0 Hz, 1H), 7.59 (s, 1H), 8.23 (s, 1H), 8.34 (d, J = 8.3 Hz, 1H) |

TABLE 1-continued

| Compound No. | R1 | R2, R3 | Y | Xm | R | $^1$H NMR (300 MHz, Solvent) |
|---|---|---|---|---|---|---|
| 3 | Me | H | H | — | Et | (CDCl$_3$) δ 1.35 (t, J = 7.1 Hz, 3H), 2.42 (s, 3H), 4.31 (q, J = 7.1 Hz, 2H), 6.89 (d, J = 5.0 Hz, 1H), 7.04 (d, J = 8.8 Hz, 2H), 7.26 (m, 3H). 7.44 (t, J = 9.0, 1H), 7.55 (s, 1H), 8.29 (s, 1H), 8.35 (d, J = 8.2 Hz, 1H) |
| 4 | Me | H | H | — | i-Pr | (CDCl$_3$) δ 1.33 (d, J = 6.2 Hz, 6H), 2.42 (s, 3H), 4.54 (m, 1H), 6.89 (d, J = 5.0 Hz, 1H), 7.04 (d, J = 8.7 Hz, 2H), 7.26 (m, 3H). 7.44 (t, J = 6.0, 1H), 7.55 (s, 1H), 8.26 (s, 1H), 8.36 (d, J = 8.3 Hz, 1H) |
| 5 | Me | H | H | — | benzyl | (CDCl$_3$) δ 2.42 (s, 3H), 5.28 (s, 2H), 6.89 (d, J = 5.0 Hz, 1H), 7.04 (d, J = 8.7 Hz, 2H), 7.35 (m, 9H), 7.53 (br, 1H), 8.36 (m, 2H) |
| 6 | Me | H | H | — | 4-F-benzyl | (CDCl$_3$) δ 2.42 (s, 3H), 5.23 (s, 2H), 6.89 (d, J = 5.0 Hz, 1H), 7.06 (m, 5H), 7.26 (m, 3H), 7.44 (m, 3H), 7.52 (br, 1H), 8.34 (m, 2H) |
| 7 | Me | H | H | — | 4-Cl-benzyl | (CDCl$_3$) δ 2.42 (s, 3H), 5.23 (s, 2H), 6.89 (d, J = 5.0 Hz, 1H), 7.04 (d, J = 8.8 Hz, 2H), 7.26 (m, 3H), 7.35 (m, 4H), 7.44 (m, 1H), 7.52 (s, 1H), 8.33 (s, 1H), 8.35 (d, J = 8.3 Hz, 1H) |
| 8 | Me | H | H | — | 4-OCH$_3$-benzyl | (CDCl$_3$) δ 2.42 (s, 3H), 3.81 (s, 3H), 5.20 (s, 2H), 6.90 (m, 3H), 7.03 (d, J = 8.8 Hz, 2H), 7.26 (m, 3H), 7.43 (m, 3H), 7.53 (br, 1H), 8.31 (s, 1H), 8.35 (d, J = 8.3 Hz, 1H) |
| 9 | Me | H | H | — | CH$_2$CF$_3$ | (CDCl$_3$) δ 2.43 (s, 3H), 4.60 (q, J = 8.5 Hz, 2H), 6.90 (d, J = 5.1 Hz, 1H), 7.07 (d, J = 9.0 Hz, 2H), 7.27 (m, 3H). 7.46 (m, 2H), 8.32 (d, J = 8.3 Hz, 1H), 8.40 (s, 1H) |
| 10 | Me | H | H | — | CH$_2$CH$_2$Cl | (CDCl$_3$) δ 2.43 (s, 3H), 3.82 (t, J = 5.9 Hz, 2H), 4.46 (t, J = 5.8 Hz, 2H), 6.90 (d, J = 5.1 Hz, 1H), 7.06 (d, J = 9.0 Hz, 2H), 7.27 (m, 3H). 7.46 (t, J = 6.0 Hz, 1H), 7.53 (s, 1H), 8.35 (d, J = 9.0 Hz, 1H), 8.60 (s, 1H) |
| 11 | Me | H | H | — | allyl | (CDCl$_3$) δ 2.43 (s, 3H), 4.74 (d, 2H), 5.3(m, 2H), 6.05 (m, 1H), 6.90 (d, J = 5.1 Hz, 1H), 7.06 (d, J = 9.0 Hz, 2H), 7.27 (m, 3H). 7.46 (t, J = 6.0 Hz, 1H), 7.53 (s, 1H), 8.35 (s, 2H) |
| 12 | Me | H | H | 4-F | Me | (CDCl$_3$) δ 2.43 (s, 3H), 4.06 (s, 3H), 6.90 (d, J = 5.0 Hz, 1H), 7.03 (m, 3H), 7.16 (m, 1H), 7.30 (d, J = 5.0 Hz, 1H), 7.41 (br, 1H), 8.25 (m, 2H) |
| 13 | Me | H | H | 4-F | t-Bu | (CDCl$_3$) δ 1.38 (s, 9H), 2.42 (s, 3H), 6.90 (d, J = 5.1 Hz, 1H), 7.00 (m, 3H), 7.15 (m, 1H), 7.30 (d, J = 5.1 Hz, 1H), 7.43 (br, 1H), 8.23 (s, 1H), 8.23 (m, 1H) |
| 14 | Me | H | H | 4-F | CH$_2$CF$_3$ | (CDCl$_3$) δ 2.43 (s, 3H), 4.59 (q, J = 8.5 Hz, 2H), 6.90 (d, J = 5.0 Hz, 1H), 7.00 (dd, J = 8.6, 3.0 Hz, 1H), 7.05 (d, J = 8.7 Hz, 2H). 7.16 (td, J = 6.0, 3.0 Hz, 1H), 7.30 (d, J = 5.0 Hz, 1H), 7.38 (s, 1H), 8.21 (dd, J = 9.1, 5.2 Hz, 1H), 8.38 (s, 1H) |
| 15 | Me | H | H | 4-F | CH$_2$CH$_2$Cl | (CDCl$_3$) δ 2.43 (s, 3H), 3.81 (t, J = 5.8 Hz, 2H), 4.46 (t, J = 5.8 Hz, 2H), 6.90 (d, J = 5.0 Hz, 1H), 7.03 (m, 3H), 7.16 (m, 1H), 7.30 (d, J = 5.0 Hz, 1H), 7.41 (br, 1H), 8.23 (m, 1H), 8.35 (s, 1H) |

Next, examples of the bioactivity assay are described.

Experimental Example 1

Wheat Rust Control Effect Test

A predetermined amount of the present compound corresponding to the test concentration was dissolved in 10% acetone and then was sprayed to foliage in a single leafy wheat (variety: Baegjoong) grown in a circular pot (6×7 cm, diameter×height). One day after application, the wheat plants were inoculated by spraying a spore suspension which was prepared with spores obtained from wheat leaves infected with wheat rust pathogen (*Puccinia recondita*). After an inoculation period of 1 day at 20° C. humid conditions, the plants were kept in a chamber for 14 days at a constant temperature and humidity under constant light conditions. After 15 days of the compound treatment, the disease incidence was assessed according to the following equation (1), and the control value was determined according to the following criteria.

Control value (%)=(1−$X/Y$)×100     (Equation 1)

here,
X: ratio of diseased leaf area of treated plants
Y: ratio of diseased leaf area of non-treated plants Criteria
0: less than 9% control value
1: Control value 10-29%
2: Control value 30-49%
3: Control value 50-69%
4: Control value 70-89%
5: Control value 90-100%

As a result of the above test, the compounds of the present invention exhibited excellent control effects with respect at the active ingredient concentration of 200 ppm and the amount of spraying dose of 30 mL, and in particular, Compound Nos. 1, 4, and 9 exhibited high activity of criterion 5.

Experimental Example 2

Rice Sheath Blight Control Effect Test

A predetermined amount of the present compound corresponding to the test concentration was dissolved in 10% acetone and then was sprayed to foliage in the 5-leaf stage rice (variety: Chucheongbyeo) grown in a circular pot (6×7 cm, diameter×height). One day after application, the rice plants were inoculated by spraying a mycelial suspension of a culture of rice sheath blight pathogen (*Rhizoctonia solani*) obtained by culturing in a rice bran culture medium and incubated to induce disease development for 5 days under a humid condition at 30° C. After 5 days of the compound treatment, the disease incidence was assessed according to the equation (1) of Experimental Example 1, and the control value was determined according to the criteria of Experimental Example 1.

As a result of the above test, the compound of the present invention exhibited an excellent control effect at the active ingredient concentration of 200 ppm and the amount of spraying dose of 30 mL, and in particular, Compound No. 1 exhibited a high activity of the criterion 5 in the above equation 1.

Experimental Example 3

Cucumber Powdery Mildew Control Effect Test

A predetermined amount of the present compound corresponding to the test concentration was dissolved in 10% acetone and then was sprayed to foliage in a single leafy cucumber (variety: Baekdadagi) grown in a circular pot (6×7 cm, diameter×height). One day after application, the Cucumber plants were inoculated by spraying a spore suspension prepared with spores obtained from cucumber leaves infected with cucumber powdery mildew pathogen (*Sphaerotheca* fusca). After an incubation period of 1 day at 20° C. humid conditions, the plants were kept in a chamber for 12 days at a constant temperature and humidity under constant light conditions. After 13 days of the compound treatment, the disease incidence was assessed according to equation (1) of Experimental Example 1, and the control value was determined according to the criteria of Experimental Example 1.

As a result of the above test, the compound of the present invention exhibits excellent control effect at the active ingredient concentration of 200 ppm and the amount of spraying dose of 30 mL, and in particular, Compound Nos. 1, 2, 3, 4, 5, 6, 7, 8, 9, 10, 11, 12, 13, and 14 showed high activity of criterion 5 in the equation 1 above.

Experimental Example 4

Cucumber *Sclerotinia* Disease Control Effect Test

A predetermined amount of the present compound corresponding to the test concentration was dissolved in 10% acetone and then was sprayed to foliage in a single leafy cucumber (cultivar: Baekdadagi) grown in a circular pot (6×7 cm, diameter×height). One day after application, the Cucumber plants were inoculated by spraying a mycelial suspension of a liquid culture of cucumber *sclerotinia* pathogen (*Sclerotinia sclerotiorum*) and incubated for 4 days under constant light conditions and high humidity conditions at 25° C. to induce disease development. Four days after the compound treatment, the disease incidence was assessed according to equation (1) of Experimental Example 1, and the control value was determined according to the criteria of Experimental Example 1.

As a result of the above test, the compound of the present invention exhibited an excellent control effect at the active ingredient concentration of 200 ppm and the amount of spraying dose of 30 mL, and in particular, Compound No. 1 exhibited a high activity of the criterion 5 in the above equation 1.

Experimental Example 5

Compound No. 1 and the following four compounds as a comparative control compound were evaluated for controlling cucumber powdery mildew as described in Experimental Example 3.

Comparative compound A: 3-(difluoromethyl)-N-(4'-((methoxyimino)methyl)-[1,1'-biphenyl]-2-yl)-1-methyl-1H-pyrazole-4-carboxamide (Compound I-11 of WO 2002/008197 A1)

Comparative compound B: N-(4'-((methoxyimino)methyl)-[1,1'-biphenyl]-2-yl)-3-methylthiophene-2-carboxamide (Compound 1-47 of WO 2002/008197 A1)

Comparative compound C: 3-(difluoromethyl)-N-(3'-fluoro-4'-((methoxyimino)methyl)-[1,1'-biphenyl]-2-yl)-1-methyl-1H-pyrazole-4-carboxamide (Compound I-114 of WO 2002/008197 A1)

Comparative compound D: 5-chloro-N-(3',5'-difluoro-4'-((methoxyimino)methyl)-[1,1'-biphenyl]-2-yl)-3-(difluoromethyl)-1-methyl-1H-pyrazole-4-carboxamide (Compound 23 of WO 2013/167550 A1)

TABLE 2

| Treatment Concentration | Activity of Compound 1 | Activity of Comparative Compound | | | |
|---|---|---|---|---|---|
| | | A | B | C | D |
| 10 ppm | 5 | 0 | 1 | 0 | 1 |

INDUSTRIAL APPLICABILITY

The compound of the present invention is useful as a plant disease control agent for agricultural and horticultural use, which has a broad control spectrum with a low drug amount against agricultural and horticultural plant diseases, and exhibits an excellent control effect.

The invention claimed is:

1. A difluoro biphenyl thiophene carboxamide compound represented by the following General Formula (I):

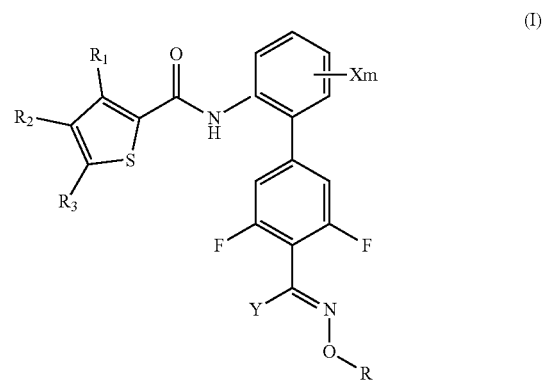

in the above Formula,
Y is a hydrogen atom or a (C1~C4)alkyl;
X is a halogen atom or a (C1~C4)alkyl;
m is an integer of 0~2;
R is a hydrogen atom, (C1~C6)alkyl, (C2~C6)alkenyl, (C2~C6)alkynyl, (C1~C6)alkyl which may be substituted by 1 to 5 halogen atoms, (C1~C3)alkyl which may be substituted with (C3~C6)cycloalkyl, (C1~C3) alkyl which may be substituted with phenyl or pyridine, phenyl(C1~C3)alkyl (which may be substituted with a halogen atom), phenyl(C1~C3)alkyl which may be substituted with (C1~C4)alkyl, or phenyl(C1~C3)alkyl which may be substituted with (C1~C4)alkoxy;
R1 is a halogen, (C1~C4)alkyl, or (C1~C4)alkyl substituted by 1 to 3 halogen atoms, and R2 and R3 are each independently hydrogen, (C1~C4) alkyl, or halogen.

2. The compound of claim 1, wherein Y is a hydrogen atom and m is 0.

3. The compound of claim 2, wherein Y is a hydrogen atom; m is 0; R is (C1~C6)alkyl, (C2~C6)alkenyl, (C2~C6)alkynyl, (C1~C6)alkyl which may be substituted by 1 to 5 halogen atoms, (C1~C3)alkyl which may be substituted with (C3~C6)cycloalkyl, (C1~C3)alkyl which may be substituted with phenyl or pyridine, phenyl(C1~C3)alkyl (which may be substituted with a halogen atom), phenyl(C1~C3)alkyl which may be substituted with (C1~C4)alkyl, or phenyl(C1~C3)alkyl which may be substituted with (C1~C4) alkoxy; R1 is (C1~C4)alkyl or (C1~C4)alkyl substituted with 1 to 3 halogen atoms; and R2 and R3 are a hydrogen atom.

4. The compound of claim 3, wherein Y is a hydrogen atom, m is 0, R is (C1~C6)alkyl or (C1~C4)alkyl which may be substituted by 1 to 3 halogen atoms; R1 is methyl, and R2 and R3 are a hydrogen atom.

5. A plant disease control agent for agricultural and horticultural use, comprising as an active ingredient the compound of the General Formula (I) according to claim 1 or a salt thereof.

6. A method for controlling a plant disease, comprising applying to a plant of interest or soil an effective amount of a compound of the General Formula (I) according to claim 1 or a salt thereof.

* * * * *